United States Patent
De Vincentiis

(10) Patent No.: US 9,302,117 B2
(45) Date of Patent: Apr. 5, 2016

(54) MEDICAL NEUROLOGICAL INSTRUMENT

(76) Inventor: Armando De Vincentiis, Milan (IT)

( * ) Notice: Subject to any disclaimer, the term of this patent is extended or adjusted under 35 U.S.C. 154(b) by 91 days.

(21) Appl. No.: 13/576,803

(22) PCT Filed: Jan. 21, 2011

(86) PCT No.: PCT/EP2011/050829
§ 371 (c)(1),
(2), (4) Date: Aug. 2, 2012

(87) PCT Pub. No.: WO2011/098339
PCT Pub. Date: Aug. 18, 2011

(65) Prior Publication Data
US 2012/0303077 A1 Nov. 29, 2012

(30) Foreign Application Priority Data
Feb. 12, 2010 (IT) .............................. MI2010A0216

(51) Int. Cl.
*A61N 5/06* (2006.01)
*A61N 1/36* (2006.01)

(52) U.S. Cl.
CPC .......... *A61N 5/0613* (2013.01); *A61N 1/36021* (2013.01); *A61N 2005/0659* (2013.01); *A61N 2005/0662* (2013.01); *A61N 2005/0663* (2013.01)

(58) Field of Classification Search
CPC ................. A61N 2005/065; A61N 2005/0658; A61N 2005/0659; A61N 2005/0663; A61N 5/06; A61N 5/0616
USPC .................................................. 607/2, 3, 46
See application file for complete search history.

(56) References Cited

U.S. PATENT DOCUMENTS 4,989,605 A * 2/1991 Rossen ........................... 607/46
7,198,633 B1 4/2007 Starwynn
(Continued)

FOREIGN PATENT DOCUMENTS

DE 102004017547 A1 10/2005
EP 0674468 A2 9/1995
(Continued)

OTHER PUBLICATIONS

International Search Report for PCT/EP2011/050829, published on Aug. 18, 2011.

*Primary Examiner* — Michael Kahelin
*Assistant Examiner* — Minh Duc Pham
(74) *Attorney, Agent, or Firm* — Allen J. Moss; Squire Patton Boggs (US) LLP

(57) ABSTRACT

The present invention relates to a medical neurological instrument which can be used to improve balance, comprising: (A) a control system for managing energy sources of different nature and (B) an emitter of said energy sources, wherein the emitter is configured to simultaneously apply the different types of energy to a patient by means of transducers, wherein the energies employed are: (i) light energy 18 with a wavelength of between 500 and 700 nm, (ii) light energy 19 with a wavelength of between 701 and 1050 nm, (iii) TENS Energy (Transcutaneous Electrical Nerve Stimulator) 20 with a maximum amplitude of 200 V.

16 Claims, 2 Drawing Sheets

(56) References Cited

U.S. PATENT DOCUMENTS

| | | |
|---|---|---|
| 2002/0143373 A1 | 10/2002 | Courtnage |
| 2004/0158300 A1 | 8/2004 | Gardiner |
| 2005/0131497 A1 | 6/2005 | Suzuki |
| 2006/0178661 A1 | 8/2006 | Neher |
| 2008/0058881 A1* | 3/2008 | Wagner et al. ............. 607/15 |
| 2008/0077198 A1 | 3/2008 | Webb |
| 2009/0043293 A1 | 2/2009 | Pankratov |
| 2010/0121419 A1* | 5/2010 | Douglas ............. 607/90 |
| 2011/0125077 A1* | 5/2011 | Denison et al. ............. 604/20 |

FOREIGN PATENT DOCUMENTS

| | | |
|---|---|---|
| WO | 90/11798 A1 | 10/1990 |
| WO | 2005/077452 A1 | 8/2005 |
| WO | 2007/109124 A2 | 9/2007 |

* cited by examiner

MEDICAL NEUROLOGICAL INSTRUMENT

CROSS-REFERENCE TO RELATED APPLICATIONS

This application is a U.S. national phase application of and claims priority to International Application PCT/EP2011/050829, filed on Jan. 21, 2011, which claims priority to and incorporates by reference Italian Application No. MI2010A000216, filed on Feb. 12, 2010.

FIELD OF THE INVENTION

The present invention relates to a medical neurological instrument, which is useful in the treatment of some important disorders, and is particularly useful in the systematic improvement of balance, especially to avoid falls of elderly people.

BACKGROUND OF THE INVENTION

The elderly are at high risk of falling, which is one of the most widespread causes of illness and even death. Mark, H. B. in *Falls. The Merck Manual of Geriatrics*, third Ed. 2000, pages 195-203, reports that at least 30% of people over 65 not living in hospitals experience falls at least once a year. Balance control is essential for performing everyday voluntary movements. Increasing age involves a higher risk of falling, due to bad posture.

Unstable balance related to age is negatively affected by possible pathological conditions and by unfavourably environmental and pharmacological conditions: in some cases even stability perception is impaired. Aizen, E., in *Cautious Gait and Fear of Falling in the Elderly* Harefuah November 2001, 140 (11): 1091 4-1115, reports that falling often involves a reduction in mobility, due to the fear of falling again. It is therefore apparent that limiting the possibility of falls would result in a great improvement of life conditions and possibly even in a longer life.

From the above it is apparent that improvement in posture control would result in a reduction of falls in elderly people. Posture control concerns all the static-dynamic processes affecting the position of a body in space and the parts of said body in reciprocal motion, maintaining the specific orientation with respect to the force of gravity. The function of the central nervous system is to transform an irregular flow of impulses into a regular activation, which is governed by suitable neuromotor nuclei.

The nervous signals that originate during motion were defined as a whole as proprioceptive sensitivity by Charles Sherrington in 1906. According to this definition, suitable stimuli are applied by the body to specific receptors, which are located within movement organs. Proprioceptive sensitivity refers to different kinds of stimuli: contact, pressure, pain. All the information collected through proprioceptors is an essential element for programming and controlling stillness and movement.

The most important proprioceptors are neuromuscular spindles and Golgi tendon organs, which are stretch receptors. Spindles are a highly specialised structure, widely distributed in the muscle parenchyma of skeletal muscles. Such a structure consists of a bundle of muscle fibres, enclosed in a capsule. Any muscle stretching is perceived by intrafusal fibres. Neuromuscular spindles are type 1 receptors, responding to energy changes with an electrical potential called "generating potential". Spindle sensitivity to stretching is very high and is extremely important in the perception of one's position and orientation. A suitable action on proprioceptors is very important to achieve good posture control.

In recent years, great efforts have been made to find the best action on proprioceptors. Kramer, A., in *Demography and Health Status*; Geriatric Medicine, Second Ed. 1996; 18-27 and Herbert, D. R. et al.; *Effective Physiotherapy* BMJ, vol. 323, pages 788-790, showed that through proprioceptive stimulation involving muscle exercises for the legs, improvement of motor performance can be achieved. However, Studenski, S., in *Guest Edition Clinics in Geriatric Medicine*, November 1996, *Gait and Balance Disorders*, 635-658, pointed out that there is no correlation between muscle strengthening and balance. In any case, muscle training is presently the most common treatment for improving balance.

OBJECT OF THE INVENTION

On the basis of the problems listed above, the object of the present invention is therefore to provide a device allowing a reduction in the likelihood of falls in the elderly, in a more rapid manner with respect to prior art techniques and without the use of invasive therapies.

DESCRIPTION OF THE INVENTION

Figure 1:
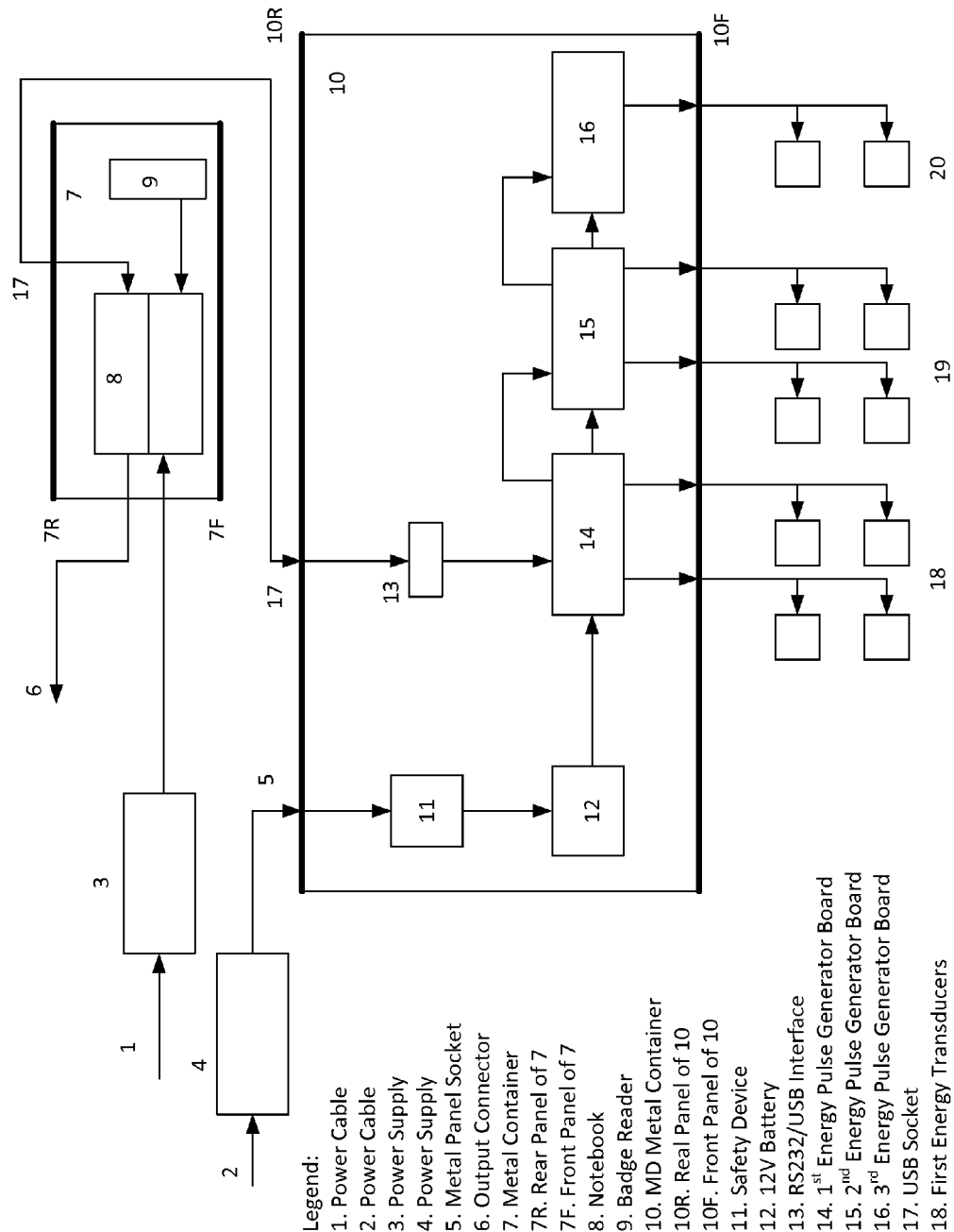
FIG. 1 illustrates a medical neurological instrument, according to certain embodiments of the present invention.

This object is achieved by the present invention through a medical neurological instrument according to claim 1.

For a better understanding of the object described herein, reference will be made to FIG. 1, in which the following components are schematically indicated:

1. power cable connected to the power supply 3, which supplies direct current voltage to charge the batteries of the notebook 8;
2. power cable connected to the power supply 4 to charge the batteries 12 of the medical device 10;
3. Notebook power supply suitable to convert the 220V mains voltage into 18V direct current to charge the battery of the notebook 8;
4. Power supply and battery charger 4 to convert the 220 Vac mains voltage into 14 volt direct current voltage to charge the battery of the MD (medical device) 10;
5. Metal panel socket mounted on the MD 10R to carry voltage into the container of the MD 10 connected to the safety device 11 which performs the function of shutting off the power of the MD 10 in the event of insertion of the plug of the power supply of the MD 10;
6. Output connector for LAN/Internet connection;
7. Metal container suitable to support or transport the notebook and the badge reader with openable compartments designed to house cables;
7R. Rear panel of the notebook container with feet and reinforcements for safe transport;
7F. Front panel of the notebook container with locks and reinforcing handles for safe transport;
8. Notebook;
9. Badge reader: used for immediate recognition or storage of the patient's data which will be stored in a database in the notebook 8;

10. MD metal container suitable to contain all the circuit boards 14, 15, 16 the safety device 11 and the battery 12, as well as the RS232—USB communication interface 13;

10R. MD 10 rear panel suitable to house the power socket 5 and the USB socket 17;

10F. MD front panel suitable to house all the light signals and connectors, mechanically interlocked, to convey, by means of connection cables, the signals supplied to the transducers 18,19,20;

11. Safety device that immediately shuts off operation of the MD 10, if the power plug from the power supply 4 is inserted during charging of the internal battery 12;

12. 12 volt battery, which is the sole power source for operation of the MD 10;

13. RS232/USB interface which transforms USB commands from the notebook 8 into communication signal for all the boards 14,15,16;

14. first energy pulse generator board 15. second energy pulse generator board 16. third energy pulse generator board 17. USB socket which, through the USB cable connected to the socket 17 positioned on the MD rear panel 10R, conveys the commands for the boards 14,15,16 through the interface 13 positioned inside the container 10

18. First energy transducers connected with cable and metal connector positioned on the panel 10F of the container 10;

19. Second energy transducers connected with cable and metal connector positioned on the panel 10F of the container 10;

20. Third energy transducers connected with cable and metal connector positioned on the panel 10F of the container 10;

With reference to what is shown in FIG. 1, it can be noted that the instrument comprises:

(A) a control system for managing energy sources of different nature and (B) an emitter of said energy sources, wherein the emitter is configured to contemporarily apply the different types of energy to a patient by means of transducers, wherein the energies employed are:

(i) light energy 18 with a wavelength between 500 and 700 nm, (ii) light energy 19 with a wavelength between 701 and 1050 nm, (iii) TENS Energy (Transcutaneous Electrical Nerve Stimulator) 20 with a maximum amplitude of 200V and wherein the control system (A), which is a computer having dedicated software, manages the strength, frequency and duration of these energies.

The emitter emits electromagnetic radiation in the form of pulses having a frequency between 0.5 and 500 Hz, preferably between 1 and 200 Hz and these pulses have two alternating discrete frequencies, wherein the first frequency is between 0 and 10 Hz and the second frequency 40 and 1500 Hz. Preferably the first frequency is between 0.5 and 5 Hz and the second frequency between 50 and 500 Hz, more preferably the first frequency is between 1 and 3 Hz and the second frequency between 80 and 200 Hz.

According to a preferred embodiment, the first frequency is 3 Hz and the second frequency is 85 Hz, or the first frequency is 2 Hz and the second frequency is 100 Hz, or the first frequency is 1 Hz and the second frequency is 180 Hz.

Figure 2:
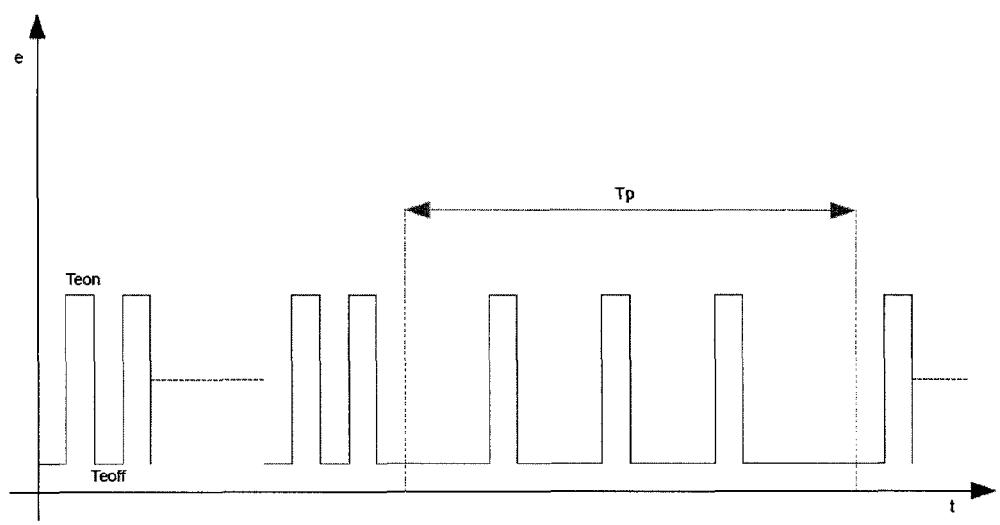
FIG. 2 illustrates a waveform applied to transducers, according to certain embodiments of the present invention.

With reference to FIG. 2, it is possible to evaluate the type of waveform applied to the transducers. The time T is represented on the abscissa, while the energy supplied e is represented on the ordinate. By varying the time Teon (on time), the time Teoff (off time) and the pause time Tp, trains of pulses are sent with variable period and duty cycle for the three energies, determined by the therapy to be performed. It is also possible to send single energy pulses during the pause time Tp.

The pulses are preferably characterized by:
an on time (Teon) of between 0.01 and 1 ms,
an off time (Teoff) of between 1 and 10 ms and
a pause time (Tp) of between 0.5 and 20 s.

The transducers (18, 19, 20) consist of semiconductive light emitters (3) with fixed emission of 2000 mcd, where these emitters are preferably divided into three groups of at least two units each, so as to repeatedly emit pulses every 2, 4 and sec respectively. The duration of the single pulse is 50-1000 μs, preferably 80-500 μs, even more preferably 90-350 μs.

According to the present invention, the electromagnetic radiation consists of an electrical current, generated by pairs of electrodes, having a maximum voltage of 240V, preferably between 50 and 85V.

As specified, the strength, frequency and duration of the pulses are controlled from the notebook 7, which, with a specifically developed software program, manages operation thereof. In order to use the device according to the present invention correctly, it is essential for the three energy sources to be used simultaneously to obtain a beneficial effect for the patient. These energies are therefore variable according to pathological condition. The present device thus allows the operator to dose the strength, frequency and duration of the pulses for each of the energy sources, obtaining a synergic combination of these sources, which can be optimised for the specific pathological conditions encountered and which can also be customized for each patient.

Interface with the Internet 6 also allows interaction and exchange of therapeutic programs, in real time, with the various experiences of the physicians using it, thus allowing the creation of a sort of interactive database in which information on each treatment can be saved, to the benefit of the next operator who wishes to receive information and advice on parameters to use. The aforesaid optimization is therefore shared and can benefit from a plurality of experimental contributions.

A preferred configuration comprises six emitters, of which two emitters repeatedly emit pulses every 2 sec., two emitters repeatedly emit pulses every 4 sec. and two emitters repeatedly emit pulses every 8 sec. In other words, the difference in the behaviour of the emitters is found only in the duration of the interval between one pulse and the next.

The emitters therefore emit a radiation in the region of the red and infrared wavelength. The useful carrier wavelength is in the interval between 400 and 1,000 nm. The best results are achieved by means of the simultaneous use of a radiation having two discrete wavelengths, the first between 450 and 700 nm and the second between 750 and 1000 nm. In particular, good results are achieved with a first wavelength between 550 and 660 nm and the second wavelength between 850 and 980 nm. The best results are achieved with a first wavelength in the interval between 580 and 645 nm and the second wavelength in the interval between 870 and 920 nm. The radiation can be monochromatic radiation, coherent or incoherent.

According to a preferred embodiment of the present invention, the electromagnetic radiation consists of an electrical current having the same frequency interval. The transducers are electrodes having a negative pole on one side and a positive pole on the other side, to be applied to the skin. The first pair of electrodes generates pulses every 2 sec., the second pair every 4 sec. and the third pair every 8 sec. The current is regulated at a voltage between 0 and 240V, preferably between 0 and 150V, more preferably between 0 and 110V. The length of each pulse is the same as indicated previously.

The medical neurological instrument according to the present invention is mainly used to reduce the likelihood of falls in the elderly, without invasive therapies. Alternatively, it can be used to alleviate pain, in particular for myofascial pain, primary and secondary trigger points and referred pain points and in benign chronic pain (secondary algo-dysfunctional syndrome), for example as in the case of osteoarthritic conditions.

When used to reduce the likelihood of falls improving balance, pulses must be applied for a time of between 30 sec. and 30 min., preferably between 45 sec. and 10 min., the strength, frequency and duration of the pulses more preferably between 1 min. and 5 min. Preferably the pulses are sent every 2 sec., but the instrument is also effective for pulses every 4 sec. Preferably, the pulses are applied to the patient's limbs. Application improves balance, also during thrust, and the effect lasts for 10 to 40 days, prevalently according to age and condition.

The instrument can be useful in pain therapy, in the same conditions, applying it also to the site of the pain for a longer time, usually between 2 min. and 2 hours, preferably between 4 min. and 30 min, more preferably between 5 min. and 15 min. It is particularly useful for alleviating pain in the cervical region, in the lumbar region and for treating osteoarthritis.

The invention will now be illustrated in greater detail with reference to some operating examples in which a series of patients of different gender and with different physical and pathological conditions were subjected to treatment with the instrument according to the present invention. A certified and validated stabilometric platform showed the improvement in static balance of patients treated. However, using a treadmill equipped with sensors, also certified and validated, known in the scientific field as gait analysis instrument, the results are much more indicative and, as can be seen in the tables below, highlighted improvement in walking velocity, step length, cadence (steps/min.) and decreased need for support of patients treated.

PATIENT 1, suffering from Alzheimer's and polyarthrosis.

| Age | Gender | Left | LEG | Right | Height | Weight |
|---|---|---|---|---|---|---|
| 79 | M | 89 | | 89 | 180 | 0 |

Measures:
From: Jun. 8, 2009 13:24:23 to Jun. 8, 2009 13:39:58

| | velocity cm/sec | mean velocity LL/sec | step length cm | double support sec | base of support cm | FAP |
|---|---|---|---|---|---|---|
| p | 45.4 | 0.51 | 32.295 | 0.507 | 17.45 | 55 |
| d | 61.5 | 0.69 | 42.656 | 0.38 | 16.76 | 75 |
| diff | 35.5% positive | 35.3% positive | 20.9% positive | 25.0% positive | 9.0% positive | positive |

| Date/time | Velocity | Cadence (step/min) | Step Length Left | Step Length Right |
|---|---|---|---|---|
| Jun. 8, 2009 13:39:58 | 61.5 | 86.5 | 41.143 | 44.546 |
| Jun. 8, 2009 13:24:23 | 45.4 | 77.3 | 34.748 | 35.733 |

Comments
Patient suffering from brain damage
Pre/post treatment comparison shows that:
walking velocity increases, with relative increase in the step length;
duration of the double support stage decreases, as does the size of the base of support, showing increased confidence in walking.

The pre/post treatment data are obtained from an average of two trials.

PATIENT 2: fibromyalgia, anxiety neurosis

| Age | Gender | Left | LEG | Right | Height | Weight |
|---|---|---|---|---|---|---|
| 52 | F | 80 | | 80 | 0 | 0 |

Measures:
From: Jun. 8, 2009 14:42:53 to Jun. 8, 2009 5:12:58

| | velocity cm/sec | mean velocity LL/sec | step length cm | double support sec | base of support cm | cadence |
|---|---|---|---|---|---|---|
| p | 77.5 | 0.97 | 51.01 | 0.345 | 5.47 | |
| d | 89.4 | 1.12 | 52.67 | 0.281 | 9.24 | |
| diff | 15.4% positive | 15.5% positive | 3.3% positive | 18.6% positive | 68.9% negative | |

| Date/time | Velocity | Cadence (step/min) | Step Length Left | Step Length Right |
|---|---|---|---|---|
| Jun. 8, 2009 15:12:58 | 89.4 | 101.8 | 52.193 | 52.908 |
| Jun. 8, 2009 14:42:53 | 77.5 | 91.2 | 51.362 | 50.675 |

Comments
Pre/post treatment comparison
increase in walking velocity and step length
decrease in the double support stage
increase in the size of the base of support in favor of improved stability PATIENT 3: osteoporosis, fractures of the vertebrae, severe polyarthrosis, recurring falls

| Age | Gender | Left | LEG | Right | Height | Weight |
|---|---|---|---|---|---|---|
| 84 | F | 73 | | 73 | 0 | 0 |

Measures:
From: Jun. 8, 2009 15:00:50 to Jun. 8, 2009 15:46:51

| | velocity cm/sec | mean velocity LL/sec | step length cm | double support sec | base of support cm | cadence |
|---|---|---|---|---|---|---|
| p | 60.5 | 0.83 | 40.752 | 0.412 | 10.81 | |
| d | 98.9 | 1.35 | 55.27 | 0.258 | 8.68 | |
| diff | 63.5% positive | 62.7% positive | 35.6% positive | 37.4% positive | 19.7% positive | |

| Date/time | Velocity | Cadence (step/min) | Step Length Left | Step Length Right |
|---|---|---|---|---|
| Jun. 8, 2009 15:46:51 | 89.4 | 107.4 | 58.07 | 51.77 |
| Jun. 8, 2009 15:00:50 | 60.5 | 89.1 | 45.068 | 38.151 |

Comments
Pre/post treatment comparison
increase in walking velocity and step length
decrease in the duration of the double support stage and size of the base of support PATIENT 4: recurring falls

| Age | Gender | Left | LEG | Right | Height | Weight |
|---|---|---|---|---|---|---|
| 52 | F | 85 | | 85 | 0 | 0 |

Measures:
From: Jun. 8, 2009 16:49:28 to Jun. 8, 2009 17:34:48

| | velocity cm/sec | mean velocity LL/sec | step length cm | double support sec | base of support cm | cadence |
|---|---|---|---|---|---|---|
| p | 85.5 | 1.01 | 54.36 | 0.294 | | 94.4 |
| d | 91.9 | 1.08 | 56.43 | 0.250 | | 97.7 |
| diff | 7.5% positive | 6.9% positive | 3.8% positive | 15.0% positive | positive | 3.5% positive |

| Date/time | Velocity | Cadence (step/min) | Step Length Left | Step Length Right |
|---|---|---|---|---|
| Jun. 8, 2009 17:34:48 | 91.9 | 97.7 | 56.811 | 56.165 |
| Jun. 8, 2009 16:49:28 | 85.5 | 94.4 | 53.959 | 54.561 |

Comments
Pre/post treatment comparison
increase in walking velocity and step length
decrease in the duration of the double support stage
size of the base of support remains the same PATIENT 5: recurring falls

| Age | Gender | Left | LEG | Right | Height | Weight |
|---|---|---|---|---|---|---|
| 83 | F | 78 | | 78 | 0 | 0 |

Measures:
From: Jun. 8, 2009 17:28:13 to Jun. 8, 2009 18:01:49

| | velocity cm/sec | mean velocity LL/sec | step length cm | double support sec | base of support cm | cadence |
|---|---|---|---|---|---|---|
| p | 46.3 | 0.59 | 33.815 | 0.495 | 11.42 | 82.1 |
| d | 52.0 | 0.67 | 34.293 | 0.433 | 12.68 | 90.9 |
| diff | 12.3% positive | 13.6% positive | 1.4% positive | 12.5% positive | 11.0% negative | 10.7% positive |

| Date/time | Velocity | Cadence (step/min) | Step Length Left | Step Length Right |
|---|---|---|---|---|
| Jun. 8, 2009 18:01:49 | 52 | 90.9 | 35.189 | 33.595 |
| Jun. 8, 2009 17:28:13 | 46.3 | 82.1 | 33.612 | 34.018 |

Comments
Pre/post treatment comparison
increase in walking velocity and step length
decrease in the duration of the double support stage
significant increase in the size of the base of support

The invention claimed is:

1. A medical neurological device comprising:
(A) a control system for managing energy sources of different natures and
(B) an emitter of said energy sources,
wherein the emitter is configured to simultaneously apply the different types of energy to a patient using transducers, wherein the energies employed are
(i) light energy with a wavelength of between 500 and 700 nm,
(ii) light energy with a wavelength of between 701 and 1050 nm, and
(iii) Transcutaneous Electrical Nerve Stimulator Energy with a maximum amplitude of 240V and wherein the control system is configured to control the strength, frequency and duration of these energies,
wherein the electromagnetic radiation of the Transcutaneous Electrical Nerve Stimulator Energy comprises an electrical current, generated b pairs of electrodes,
wherein the emitter is configured to emits electromagnetic radiation in the form of pulses having two alternating discrete frequencies,
wherein the first frequency is 3 Hz and the second frequency is 85 Hz, or the first frequency is 2 Hz and the second frequency is 100 Hz, or the first frequency is 1 Hz and the second frequency is 180 Hz;
wherein the transducers comprise light emitters with a fixed emission of 2000 mcd, and said light emitters are arranged into three groups of at least two emitters per group, so that they repeatedly emit pulses every 2, 4 and 8 seconds respectively;
wherein the pulses are characterized by an on time of between 0.01 and 1 ms, an off time of between 1 and 10 ms and a pause time of between 0.5 and 20 s.

2. The medical neurological instrument according to claim 1, wherein each pulse has a duration of between 50 and 1000 µs.

3. The medical neurological instrument according to claim 1, wherein each pulse has a duration of between 80 and 500 µs.

4. The medical neurological instrument according to claim 1, wherein each pulse has a duration of between 90 and 350 µs.

5. The medical neurological instrument according to claim 1, wherein the current has a maximum voltage of 200V.

6. The medical neurological instruments according to claim 1, wherein the current has a maximum voltage between 50 and 85V.

7. The medical neurological instrument according to claim 1, wherein the control system is a computer running dedicated software.

8. The medical neurological instrument of claim 1, further comprising a stabilometric platform.

9. A method of treating a patient disorder, the method comprising:
providing a medical neurological device according to claim 1, and applying the emitter of the device to the patient.

10. The method of claim 9, wherein the patient suffers from a balance disorder and the pulses are applied for 30 s to 30 m.

11. The method of claim 10, wherein the pulses are applied between 1 min and 4 min.

12. The method of claim 11, wherein the pulses are applied to the patient's limbs at a frequency of 2 to 4 s.

13. The method of claim 9, wherein the disorder comprises at least one of myofascial pain, cervical pain, primary and secondary trigger points and referred pain points, or secondary algo-dysfunctional syndrome.

14. The method of claim 13, wherein the pulses are applied to a site of the pain for a time of 2 minutes to 2 hours.

15. The method of claim 13, wherein the pulses are applied to a site of the pain for a time of 4 minutes to 30 minutes.

16. The method of claim 9, further comprising providing a stabilometric platform.

\* \* \* \* \*